United States Patent [19]

Neri et al.

[11] 4,022,813

[45] May 10, 1977

[54] METHOD FOR THE PREPARATION OF SALTS OF CARBONIC ACID MONOESTERS

[75] Inventors: Carlo Neri; Gioacchino Cipriani, both of San Donato Milanese, Italy

[73] Assignee: ANIC, S.p.A., Palermo, Italy

[22] Filed: Dec. 10, 1975

[21] Appl. No.: 639,443

[30] Foreign Application Priority Data

Dec. 10, 1974 Italy .................................. 30339/74

[52] U.S. Cl. ............................................. 260/463
[51] Int. Cl.² ......................................... C07C 68/00
[58] Field of Search ..................................... 260/463

[56] References Cited

UNITED STATES PATENTS 3,445,497  5/1969  Anderson et al. ................ 260/463

*Primary Examiner*—Lewis Gotts
*Assistant Examiner*—D. R. Phillips
*Attorney, Agent, or Firm*—Ralph M. Watson

[57] ABSTRACT

A method is disclosed for preparing salts of monoesters of the carbonic acid, the improvement consisting in that the alcohol corresponding to the monoester is reacted with carbon dioxide and a halide of a metal of the Groups IA, IIA, IIIA and IIB of the Periodic Table, the reaction being effected in the presence of a nitrogenous, aliphatic, aromatic or heterocyclic base.

8 Claims, No Drawings

METHOD FOR THE PREPARATION OF SALTS OF CARBONIC ACID MONOESTERS

This invention relates to a method for preparation of salts of monoesters of the carbonic acid, having the formula:

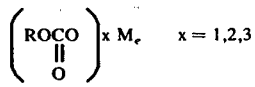   x = 1,2,3 wherein R is an alkyl, aryl, cycloalkyl or aralkyl radical, either saturated or unsaturated, substituted or unsubstituted; either mono- or poly-hydroxylated and Me is a metal of the Groups IA, IIA, IIIA and IIB of the Periodic Table, by reaction of the corresponding alcohols with carbon dioxide and a halide of said metals, in the presence of nitrogenous, aliphatic, aromatic and heterocyclic bases. The reaction is described by the equation:

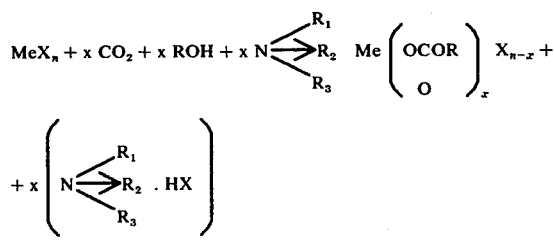

wherein $R_1$, $R_2$, $R_3$ can be hydrogen, alkyl, aryl, either substituted or unsubstituted, either saturated or unsaturated and $n$ is 1, 2, 3.

Among the metal halides LiCl, NaCl, KCl, $CaCl_2$, $MgCl_2$, $ZnCl_2$ and others lend themselves well and, among the nitrogenous bases, ammonia, propylamine, triethylamine, piridine and others.

The reaction takes place by causing a stream of carbon dioxide to bubble through a solution or a suspension of the selected salt in the selected alcohol, in the presence of the amine the function of which is to bind the hydrogen halide. A pressure of $CO_2$ between 0 and 100 atmospheres is used.

The temperature is maintained between the freezing point temperature of the alcohol or the nitrogenous base and the boiling point of same, preferably between 0° and 60° C. The reaction can be carried out in the presence of any solvent whatsoever provided that it is inert towards the reaction concerned.

The salts of the monoesters of the carbonic acid can be separated from the halohydrides of the nitrogenous bases merely by filtration of the halohydride which is generally less soluble in the reaction medium and subsequent evaporation of the solvent or by fractional precipitation with an appropriate solvent.

The salts of the monoesters of carbonic acid as prepared according to the present invention can be employed in lieu of the corresponding alcoholates in the condensation reactions, for example in the condensations of aldehydes with molecules containing active hydrogens, or of esters with urea, or as catalysts in the aromatic aldehydes disproportionation reactions.

Over the alcoholates, the salts in question have a less drastic action during progress of the above indicated reactions, the side-reactions are limited and lower costs are obtained.

The practical procedures will become more clearly apparent from a scrutiny of the ensuing illustrative examples, which, however, are not to be construed as limitations to the invention.

EXAMPLE 1

3.86 grams of LiCl are dissolved in 50 mls of a 2 N methanol solution of ammonia. $CO_2$ is bubbled through the solution until the absorption has been completed, with a vigorous stirring. The reaction is quick, exothermic and complete within a few minutes. During the absorption of $CO_2$ there is precipitation of $NH_4Cl$. The hydrochloride is filtered off, the solvent evaporated and 7.05 grams of

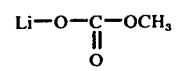

are recovered.

EXAMPLE 2

5.85 grams of NaCl are slurried in 50 mls of $CH_3OH$, containing 12 grams of $Et_3N$. $CO_2$ is caused to become absorbed by this suspension. The reaction is completed within 30 mins. approx. The solid precipitate is collected on a filter: 7.55 grams of

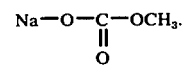

Triethylammonium chloride is recovered from the mother liquors by evaporating off the solvent.

What we claim is:

1. A method for the preparation of a salt of a monoester of carbonic acid having the formula:

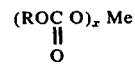

wherein R is alkyl, Me is a metal belonging to one of Groups IA, IIA, IIIA and IIB of the Periodic Table and $x$ is 1, 2 or 3, which consists in reacting the corresponding alcohol with carbon dioxide and a halide of said metal, in the presence of a nitrogenous base.

2. A method as claimed in claim 1, wherein the reaction is carried out under a $CO_2$ pressure in the range of from 0 to 100 atmospheres.

3. A method as claimed in claim 1, wherein the reaction is carried out at a temperature in the range between the freezing point temperature and the boiling point temperature of the alcohol or of the nitrogenous base.

4. A method as claimed in claim 1, wherein the reaction is carried out in the temperature range between 0° and 60° C.

5. A method as claimed in claim 1, wherein the reaction is carried out in the presence of alcohol only as the reaction medium.

6. A method as claimed in claim 1, wherein the reaction is carried out in the presence of a solvent which is inert during the reaction.

7. A method as claimed in claim 1, wherein said salt is

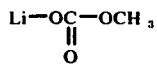
said alcohol is methanol, said nitrogenous base is ammonia, and said halide is lithium chloride.
8. A method as claimed in claim 1, wherein said salt is
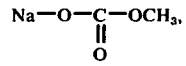
said alcohol is methanol, said nitrogenous base is triethyl amine, and said halide is sodium chloride.
* * * * *